(12) United States Patent
Wraith et al.

(10) Patent No.: US 9,775,880 B2
(45) Date of Patent: *Oct. 3, 2017

(54) METHODS OF USING MYELIN BASIS PROTEIN PEPTIDE COMPOSITIONS

(71) Applicant: APITOPE TECHNOLOGY (BRISTOL) LIMITED, Bristol (GB)

(72) Inventors: David Wraith, Bristol (GB); Heather Streeter, Bristol (GB)

(73) Assignee: APITOPE TECHNOLOGY (BRISTOL) LIMITED, Bristol (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/173,018

(22) Filed: Jun. 3, 2016

(65) Prior Publication Data

US 2016/0263188 A1    Sep. 15, 2016

Related U.S. Application Data

(60) Continuation of application No. 14/099,463, filed on Dec. 6, 2013, now Pat. No. 9,381,234, which is a division of application No. 12/740,976, filed as application No. PCT/GB2008/003673 on Oct. 30, 2008, now Pat. No. 8,623,827.

(30) Foreign Application Priority Data

Oct. 31, 2007 (GB) .................................. 0721430.7
Jan. 18, 2008 (GB) .................................. 0800962.3

(51) Int. Cl.
| | |
|---|---|
| A61K 38/10 | (2006.01) |
| A61K 38/17 | (2006.01) |
| A61K 38/39 | (2006.01) |
| A61K 39/00 | (2006.01) |
| A61K 35/30 | (2015.01) |
| C07K 7/08 | (2006.01) |
| C07K 14/47 | (2006.01) |

(52) U.S. Cl.
CPC .......... *A61K 38/1709* (2013.01); *A61K 38/10* (2013.01); *A61K 38/39* (2013.01); *A61K 39/0008* (2013.01); *A61K 35/30* (2013.01); *A61K 39/0007* (2013.01); *A61K 2039/55516* (2013.01); *C07K 7/08* (2013.01); *C07K 14/4713* (2013.01)

(58) Field of Classification Search
None
See application file for complete search history.

(56) References Cited

U.S. PATENT DOCUMENTS

| | | |
|---|---|---|
| 5,817,629 A | 10/1998 | Warren et al. |
| 8,623,827 B2 | 1/2014 | Wraith et al. |
| 2014/0161832 A1 | 6/2014 | Wraith et al. |

FOREIGN PATENT DOCUMENTS

| | | |
|---|---|---|
| EP | 1731912 A2 | 12/2006 |
| WO | WO-02/16410 A2 | 2/2002 |
| WO | WO-02/060917 A2 | 8/2002 |
| WO | WO-03/064464 A1 | 8/2003 |

OTHER PUBLICATIONS

Akdis et al., Role of interleukin 10 in specific immunotherapy. *J. Clin. Invest.* 102: 98-106 (1998).
Anderton et al., Hierarchy in the ability of T cell epitopes to induce peripheral tolerance to antigens from myelin. *Eur. J. Immunol.* 28: 1251-61 (1998).
ATX-MS1467 vaccine. Apitope International Press Release, <<http://www/apitope.com/apitopepress_03.html>>, dated Feb. 6, 2007.
Burkhart et al., Peptide-induced T cell regulation of experimental autoimmune encephalomyelitis: a role for IL-10. *Int. Immunol.* 11: 1625-34 (1999).
Cherian et al., Lyophilisation of biological. *Bioprocessing Biopartnering*, 20-21 (2006).
Chou et al., Monoclonal antibodies to human myelin basic protein. *J. Neurochem.* 46:47-53 (1986).
Giovannoni et al., Neutralising antibodies to interferon beta during the treatment of multiple sclerosis. *J. Neurol. Neurosurg. Psychiarty*, 73: 465-9 (2002).
Haines et al., Linkage of the MHC to familial multiple sclerosis suggests genetic heterogeneity. The Multiple Sclerosis Genetics Group. *Hum. Mol. Genet.* 7: 1229-34 (1998).
International Preliminary Report on Patentability, PCT/GB2008/003673, dated May 4, 2010.
International Search Report and Written Opinion of the International Searching Authority, PCT/GB2008/003673, European Patent Office, dated May 4, 2010.
Kamholz et al., Identification of three forms of human myelin basic protein by cDNA cloning. *Proc. Natl. Acad. Sci. USA*, 83:4962-6 (1986).
Liu et al., Affinity for class II MHC determines the extent to which soluble peptides tolerize autoreactive T cells in naive and primed adult mice—implications for autoimmunity. *Int. Immunol.* 7:1255-63 (1995).
Madsen et al., A humanized model for multiple sclerosis using HLA-DR2 and a human T-cell receptor. *Nat. Genet.* 23:343-7 (1999).
Medveczky et al., Myelin basic protein, an autoantigen in multiple sclerosis, is selectively processed by human trypsin 4. *FEBS Lett.* 580: 545-52 (2006).

(Continued)

*Primary Examiner* — Robert C Hayes
(74) *Attorney, Agent, or Firm* — Marshall, Gerstein & Borun LLP (57) ABSTRACT

The present invention relates to a composition which comprises the following myelin basic protein peptides: MBP 30-44; MBP 83-99; MBP 131-145; and MBP 140-154. The composition may be used to treat a disease, in particular multiple sclerosis and/or optical neuritis and the invention also relates to such uses and methods.

6 Claims, 8 Drawing Sheets

(56) References Cited

OTHER PUBLICATIONS

Metzler et al., Inhibition of experimental autoimmune encephalomyelitis by inhalation but not oral administration of the encephalitogenic peptide: influence of MHC binding affinity. *Int. Immunol.* 5:1159-65 (1993).
Muller et al., Successful immunotherapy with T-cell epitope peptides of bee venom phospholipase A2 induces specific T-cell anergy in patients allergic to bee venom. *J. Allergy Clin. Immunol.* 101:747-54 (1998).
Nepom et al., MHC class-II molecules and autoimmunity. *Ann. Rev. Immunol.* 9: 493-525 (1991).
Parker et al., Scheme for ranking potential HLA-A2 binding peptides based on independent binding of individual peptide sidechains. *J.Immunol.* 152:163-75 (1994).
Prous Science Integrity, ATX-MS1467 vaccine cleared for U.K. phase I study in MS, Prous Science, <<http://intearity.prous.com/integrity/servlet/xmlxsl/pk_qcksrch.show_records?sessionID=1&history=&query=ATX-MS-1467&abbreviation=PRO&language=en>>, dated Feb. 9, 2007.
Roberge et al., A strategy for a convergent synthesis of N-linked glycopeptides on a solid support. *Science*, 269: 202-4 (1995).
Roth et al., Evidence for the expression of four myelin basic protein variants in the developing human spinal cord through cDNA cloning. *J. Neurosci. Res.* 17:321-8 (1987).
Sundstedt et al., Role for IL-10 in suppression mediated by peptide-induced regulatory T cells in vivo. *J. Immunol.* 170:1240-8 (2003).
Mazza et al., Diversity and dynamics of the T-cell response to MBP in DR2+ve individuals, *Clin Exp Immunol*, 128:538-47 (2002).

METHODS OF USING MYELIN BASIS PROTEIN PEPTIDE COMPOSITIONS

This application is a continuation of U.S. patent application Ser. No. 14/099,463, filed Dec. 6, 2013, which is a divisional of U.S. patent application Ser. No. 12/740,976, having a 35 USC 371(c) date of Jul. 21, 2010, which is the U.S. National Stage of International Application No. PCT/GB2008/003673, incorporated by reference, filed Oct. 30, 2008, which claims priority benefit of Great Britain Application No. 0721430.7, filed Oct. 31, 2007, and Great Britain Application No. 0800962.3, filed Jan. 18, 2008.

The present invention relates to a composition which comprises myelin basic protein peptides. The composition may be used for the treatment of multiple sclerosis.

INTRODUCTION

Multiple Sclerosis

Multiple Sclerosis (MS) is the most common disabling neurological condition affecting young adults. Around 85,000 people in the UK have MS.

In multiple sclerosis (MS), inflammation of nervous tissue causes loss of myelin, a fatty material that acts as a protective insulation for nerve fibres in the brain and the spinal cord. This loss of myelin, or demyelination, leaves multiple areas of scar tissue, or sclerosis, along nerve cells. Consequently, the sclerosis results in multiple and varied neurological signs and symptoms, usually with repeated relapse and remission.

Common symptoms of MS include reduced or loss of vision, stumbling and uneven gait, slurred speech, as well as urinary frequency and incontinence. In addition, MS can cause mood changes and depression, muscle spasms and severe paralysis.

It is now generally accepted that MS is an autoimmune disease mediated by autoreactive T-cells.

Current treatments for MS generally suppress the immune system. For example, one treatment includes transplantation of bone marrow along with administration of cytostatics and immunosuppressive drugs. This treatment is effective for some patients, but it is expensive and relatively high-risk. Additionally, the administration of cytostatics is considered controversial in treating MS because its effects are unclear and potential side-effects are severe.

Treatment with interferon-beta (IFNβ) reduces the symptoms of MS in some patients and is therefore widely used. However, the mechanism of action of interferon-beta is unclear and IFNβ treatment is ineffective for many patients. Furthermore, treatment with IFNβ is compounded by the development of anti-IFNβ antibodies in most patients Giovannoni, G., Munschauer, F. E., 3rd, and Deisenhammer, F. (2002). Neutralising antibodies to interferon beta during the treatment of multiple sclerosis. J Neurol Neurosurg Psychiatry 73, 465-469.

Currently, an effective treatment for MS does not exist. Treatment is focused on merely reducing its symptoms, usually by general suppression of the immune system. There is thus an acute need for a therapy which specifically targets local immune responses associated with onset and progression of the disease.

Synthetic Peptides

Metzler and Wraith (Int. Immunol. 5:1159-1165 (1993)) were the first researchers to describe the use of synthetic peptides to induce suppression of an autoimmune response in the mouse experimental autoimmune encephalomyelitis (EAE) model, a commonly used in vivo model of MS. In this study, peptides derived from MBP were administered by the intranasal route, and it was found that the level of disease suppression correlated with the antigenic strength of the peptide used.

Later, in 1995, Liu and Wraith (Int. Immunol. 7:1255-1263) showed that it was also possible to induce suppression of EAE in mice by the intraperitoneal administration of soluble MBP-derived peptides. In this study, suppression of both Th1 and Th2 responses was achieved, and it was shown that administration of peptides after the start of an immune response could lead to suppression of the on-going immune reaction.

However, it was found that not all peptides capable of acting as T-cell epitopes are capable of inducing tolerance. The myelin basic protein (MBP) peptide 89-101 is an immunodominant antigen after immunisation and is also a very effective immunogen both in terms of priming for T cell reactivity and induction of EAE. However, this peptide has been shown to be ineffective at inducing tolerance when administered in solution (Anderton and Wraith (1998) Eur. J. Immunol. 28:1251-1261).

The present inventors have previously shown that there is a link between the capacity of a peptide to bind to an MHC class I or II molecule and be presented to a T cell without further antigen processing and its capacity to induce tolerance in vivo. Peptides which are antigen processing independent (i.e. do not require further antigen processing to bind MHC) can be predicted to be tolerogenic in vivo. These peptides have been termed "apitopes", for Antigen Processing Independent epiTOPES.

WO 02/16410 describes the following apitopes from myelin basic protein (MBP): 30-44, 80-94, 83-99, 81-95, 82-96, 83-97, 84-98, 110-124, 130-144, 131-145, 132-146 and 133-147.

WO 03/064464 identifies the following MBP peptides as being apitopes: 134-148; 135-149; 136-150; 137-151; 138-152 and 140-154.

SUMMARY OF THE INVENTION

The present inventors have now found that a "cocktail" of four MBP peptides, all of which are apitopes, is particularly effective in treating MS. It is thought that the four peptides may exert a synergistic effect when in combination.

In a first aspect, therefore, the present invention relates to a composition which comprises the following myelin basic protein peptides:

MBP 30-44;
MBP 83-99;
MBP 131-145; and
MBP 140-154.

The composition may consist essentially of MBP 30-44, 83-99, 131-145 and 140-154.

The composition may be used for treating or preventing a disease, in particular multiple sclerosis.

The composition may be used for treating or preventing optic neuritis, in particular optic neuritis associated with multiple sclerosis.

In a second aspect, the present invention relates to a method of treating or preventing multiple sclerosis and/or optic neuritis by administering a composition according to the first aspect of the invention to a subject.

In the method of the second aspect of the invention the composition may be administered following a dose-escalation protocol.

It has been found that two of the peptides in the cocktail are HLA-DQ6 binding (MBP 30-44 and 131-145) and two are HLA-DR2 binding (MBP 140-154 and 83-99). The combined use of these apitopes provides more widespread cover of the different Major Histocompatibility Complex (MHC) haplotypes seen in MS patients than therapy with a single peptide.

The method of the second aspect of the invention may involve administration of the composition to a HLA-DQ6 or HLA-DR2 positive subject.

In a third aspect, the present invention provides a kit which comprises the following myelin basic protein peptides:
MBP 30-44;
MBP 83-99;
MBP 131-145; and
MBP 140-154
for simultaneous, separate or sequential administration.

DETAILED DESCRIPTION

The first aspect of the invention relates to a composition which comprises a plurality of peptides from myelin basic protein.

Myelin Basic Protein

Myelin basic protein (MBP) is an 18.5 kDa protein isolatable from human brain white matter. The mature protein has 170 amino acids and the sequence is widely available in the literature (see for example: Chou et al (1986) J. Neurochem. 46:47-53, FIG. 1; Kamholz et al (1986), PNAS 83:4962-4966, FIG. 2; U.S. Pat. No. 5,817,629, SEQ ID NO: 1; Roth et al (1987), J. Neurosci. Res. 17:321-328, FIG. 4; Medeveczky et al (2006), FEBS Letters 580:545-552, FIG. 3B).

MBP Peptides

The term "peptide" is used in the normal sense to mean a series of residues, typically L-amino acids, connected one to the other typically by peptide bonds between the α-amino and carboxyl groups of adjacent amino acids The term includes modified peptides and synthetic peptide analogues.

The peptides used in the composition and kit of the present invention may be made using chemical methods (Peptide Chemistry, A practical Textbook. Mikos Bodansky, Springer-Verlag, Berlin.). For example, peptides can be synthesized by solid phase techniques (Roberge J Y et al (1995) Science 269: 202-204), cleaved from the resin, and purified by preparative high performance liquid chromatography (e.g., Creighton (1983) Proteins Structures And Molecular Principles, WH Freeman and Co, New York N.Y.). Automated synthesis may be achieved, for example, using the ABI 43 1 A Peptide Synthesizer (Perkin Elmer) in accordance with the instructions provided by the manufacturer.

The peptide may alternatively be made by recombinant means or by cleavage from a longer polypeptide. For example, the peptide may be obtained by cleavage from full length MBP. The composition of a peptide may be confirmed by amino acid analysis or sequencing (e.g., the Edman degradation procedure).

The peptides used in the compositions and kits of the present invention are as follows:

MBP 30-44:
H-Pro-Arg-His-Arg-Asp-Thr-Gly-Ile-Leu-Asp-Ser-Ile-Gly-Arg-Phe-NH$_2$

MBP 83-99:
H-Glu-Asn-Pro-Val-Val-His-Phe-Phe-Lys-Asn-Ile-Val-Thr-Pro-Arg-Thr-Pro-NH$_2$

MBP 131-145:
H-Ala-Ser-Asp-Tyr-Lys-Ser-Ala-His-Lys-Gly-Phe-Lys-Gly-Val-Asp-NH$_2$

MBP 140-154:
H-Gly-Phe-Lys-Gly-Val-Asp-Ala-Gln-Gly-Thr-Leu-Ser-Lys-Ile-Phe-NH$_2$

The terms "MBP 30-44", "MBP 83-99", "MBP 131-145" and "MBP 140-154" encompasses modified peptides. For example the peptides may be mutated, by amino acid insertion, deletion or substitution, so long as the MHC binding-specificity of the unmodified peptide is retained, together with its capacity to be presented to a T cell. The peptide may, for example, have 5, 4, 3, 2, 1 or 0 mutations from the unmodified sequence.

Alternatively (or in addition) modifications may be made without changing the amino acid sequence of the peptide. For example, D-amino acids or other unnatural amino acids can be included, the normal amide bond can be replaced by ester or alkyl backbone bonds, N- or C-alkyl substituents, side chain modifications, and constraints such as disulphide bridges and side chain amide or ester linkages can be included. Such changes may result in greater in vivo stability of the peptide, and a longer biological lifetime.

Modification of epitopes may be performed based on predictions for more efficient T-cell induction derived using the program "Peptide Binding Predictions" devised by K. Parker (NIH) which may be found at http://www-bimas.d-crt.nih.gov/cgi-bin/molbio/ken_parker_comboform (see also Parker, K. C et al. 1994. J. Immunol. 152:163).

MBP peptides may be formulated into the composition as neutral or salt forms. Pharmaceutically acceptable salts include the acid addition salts (formed with free amino groups of the peptide) and which are formed with inorganic acids such as, for example, hydrochloric or phosphoric acids, or such organic acids such as acetic, oxalic, tartaric and maleic. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine and procaine.

Composition

The composition of the present invention may be for prophylactic or therapeutic use.

The composition may by prepared as an injectable, either as liquid solution or suspension; solid form suitable for solution in, or suspension in, liquid prior to injection may also be prepared. The preparation may also be emulsified, or the peptides encapsulated in liposomes. The active ingredients may be mixed with excipients which are pharmaceutically acceptable and compatible with the active ingredient. Suitable excipients are, for example, water, saline (for example, phosphate-buffered saline), dextrose, glycerol, ethanol, or the like and combinations thereof.

In addition, if desired, the composition may contain minor amounts of auxiliary substances such as wetting or emulsifying agents and/or pH buffering agents. Buffering salts include phosphate, citrate, acetate. Hydrochloric acid and/or sodium hydroxide may be used for pH adjustment. For stabilisation, disaccharides may be used such as sucrose or trehalose.

In the composition, the relative ratio of the peptides (MBP 30-44:MBP 83-99:MBP 131-145:MBP 140-154) may be approximately 1:1:1:1. Alternatively the relative ratios of each peptide may be altered, for example, to focus the tolerogenic response on a particular sub-set of autoreactive T-cells or if it is found that one peptide works better than the others in particular HLA types.

After formulation, the composition may be incorporated into a sterile container which is then sealed and stored at a low temperature, for example 4° C., or it may be freeze-dried.

Conveniently the composition is prepared as a lyophilized (freeze dried) powder. Lyophilisation permits long-term storage in a stabilised form. Lyophilisation procedures are well known in the art, see for example http://www.device-link.com/ivdt/archive/97/01/006.html. Bulking agents are commonly used prior to freeze-drying, such as mannitol, dextran or glycine.

The composition may be administered in a convenient manner such as by the oral, intravenous (where water soluble), intramuscular, subcutaneous, sublingual, intranasal, intradermal or suppository routes or implanting (e.g. using slow release molecules).

The composition may advantageously be administered via intranasal, subcutaneous or intradermal routes.

The method and pharmaceutical composition of the invention may be used to treat a human subject. Typically, a physician will determine the actual dosage which will be most suitable for an individual subject and it will vary with the age, weight and response of the particular patient.

In a preferred embodiment a "dose escalation" protocol may be followed, where a plurality of doses is given to the patient in ascending concentrations. Such an approach has been used, for example, for phospholipase A2 peptides in immunotherapeutic applications against bee venom allergy (Müller et al (1998) J. Allergy Clin Immunol. 101:747-754 and Akdis et al (1998) J. Clin. Invest. 102:98-106).

Kits

Conveniently, the four MBP peptides may be administered together, in the form of a mixed composition or cocktail. However, there may be circumstances in which it is preferable to provide the peptides separately in the form of a kit, for simultaneous, separate, sequential or combined administration.

For example, the kit may comprise the four peptides in separate containers, or two containers, each comprising two peptides. The contents of the containers may or may not be combined prior to administration.

The kit may also comprise mixing and/or administration means (for example a vapouriser for intranasal administration; or a syringe and needle for subcutaneous/intradermal dosing). The kit may also comprise instructions for use.

The pharmaceutical composition or kit of the invention may be used to treat and/or prevent a disease.

In particular, the composition/kit may be used to treat and/or prevent multiple sclerosis and/or optical neuritis.

Multiple Sclerosis

Multiple Sclerosis (MS) is the most common neurological disorder among young adults (20 to 40 years old) affecting around 385,000 people in Europe and 300,000 in the USA. It is a chronic degenerative disease of the central nervous system in which gradual destruction of myelin occurs in patches throughout the brain and/or spinal cord, interfering with neural connectivity and causing muscular weakness, loss of coordination and speech and visual disturbances.

After 10 years, about half of the individuals who are initially diagnosed with Relapsing-Remitting MS (RRMS) find that the frequency of relapses decreases but disability increases. This is known as Secondary Progressive MS (SPMS). Some estimates are that within 25 years, about 90% of people with RRMS will progress to the secondary-progressive type. As with RRMS, Secondary Progressive MS can vary widely. For some patients, the increase or progression of disability is very gradual, and for others it can occur more quickly. In general, however, recovery from attacks become less and less complete, and symptoms tend to increase and disability grows. Clinical attacks become less pronounced and remissions tend to disappear, but more CNS tissue has now been destroyed and the cumulative damage is more apparent on MRI's.

The composition of the invention may be used to treat a patient with recent-onset MS, RRMS or SPMS.

The composition of the present invention may reduce or ameliorate one or more of the symptoms of MS, which include reduced or loss of vision, stumbling and uneven gait, slurred speech, urinary frequency and incontinence, mood changes and depression. SPMS can be associated with muscle spasms and severe paralysis.

In particular the composition may ameliorate optical neuritis.

Optical Neuritis

Optic Neuritis (ON) is an inflammation, with accompanying demyelination, of the optic nerve serving the retina of the eye. It is a variable condition and can present with any of the following symptoms: blurring of vision, loss of visual acuity, loss of some or all colour vision, complete or partial blindness and pain behind the eye.

Optic Neuritis is one of the most frequently presenting symptoms of multiple sclerosis and is the most common symptom at onset of MS. ON can, however, be attributable to causes other than MS, such as ischemic optic neuropathy.

ON presents unilaterally (in one eye only) in 70% of cases.

Most typically, Optic Neuritis first affects people aged between 15 and 50 years of age. In this age group, studies indicate that more than 50% of patients will convert to Multiple Sclerosis within 15 years. As with MS, women are about twice as likely as men to present with ON and the prevalence in Caucasian peoples is higher than in other racial groups.

The main symptoms of Optic Neuritis are:
Loss of visual acuity (blurring of vision).
Eye pain.
Dyschromatopsia (reduced colour vision).
Movement and sound phosphenes (visual flashing sensations brought about by side-to-side eye movement or sound).
Uhthoff's symptom, the worsening of symptoms with heat or exhaustion.

Treatment of ON with a composition according to the present invention may prevent, reduce or ameliorate any of these symptoms. In order to monitor progression of ON, visual acuity may conveniently be measured using a Snellens chart.

EXAMPLES

The following examples serve to illustrate the present invention, but should not be construed as a limitation thereof. The invention particularly relates to the specific embodiments described in these examples.

For the purpose of the Examples, the following names may be used for the MBP peptides:

| MBP peptide | Name in Examples (interchangeable) | |
| --- | --- | --- |
| 30-44 | ATX-MS-01 | Apitope MS1 |
| 83-99 | ATX-MS-07 | Apitope MS7 |
| 131-145 | ATX-MS-04 | Apitope MS4 |
| 140-154 | ATX-MS-06 | Apitope MS6 |

The composition of four peptides is termed ATX-MS-1467

Example 1 Identification of HLA-DQ6 Restricted Myelin Basic Protein T-Cell Epitopes MHC Class II genes confer susceptibility to multiple sclerosis (Nepom and Ehrlich (1991) Ann. Rev. Immunol. 9: 493-525). Within Caucasians in Northern and Central Europe, Australia and Northern America the association is linked to the MHC molecule HLA-DR2 (DR2a [DRB5*0101] and DR2b [DRB1*1501], Haines et al (1998) Human Mol. Genet. 7: 1229-1234). Although the DR2 and DQ6 alleles of MHC are found at different loci, there is significant linkage disequilibrium between the two alleles. The concordance between the two alleles is 99%, much greater than expected if the alleles were randomly re-associated. Therefore the possibility arises that certain T-cell epitopes associated with MS may be HLA-DQ6 restricted rather than HLA-DR2 restricted.

The aim of this study was to identify whether human MBP T-cell epitopes are presented by the HLA-DQ6 molecule to T-cell clones isolated from HLA-DR2 positive MS patients. T-cell activation was measured by T-cell proliferation using [$^3$H]-Thymidine incorporation.

Peptide Antigens

MBP peptides 30-44, 130-144 and 139-153 were synthesized using L-amino acids and standard F-moc chemistry on an Abimed AMS 422 multiple peptide synthesiser.

Antigen Presenting Cells

L-cells transfected with either HLA-DQ6, HLA-DR2a or HLA-DR2b, or Mgar cells (EACC, Porton Down, UK) which express HLA-DQ, DP and DR were used as APCs.

T-Cell Clones

T-cell clones MS 49:D3 and MS 17:A2 were generated from MS patients and clone N5:19 was generated from a normal individual. All three clones were isolated from DR2 positive individuals.

Antigen Presentation Assay

Antigen presenting cells were incubated with the various concentrations of peptide and the appropriate T-cells. Proliferation, and therefore activation, of the T-cells was measured by [$^3$H]-Thymidine incorporation, and expressed as the stimulation index (SI=corrected counts per minute (ccpm) culture containing peptide/ccpm culture without peptide).

Results

Figure 1:
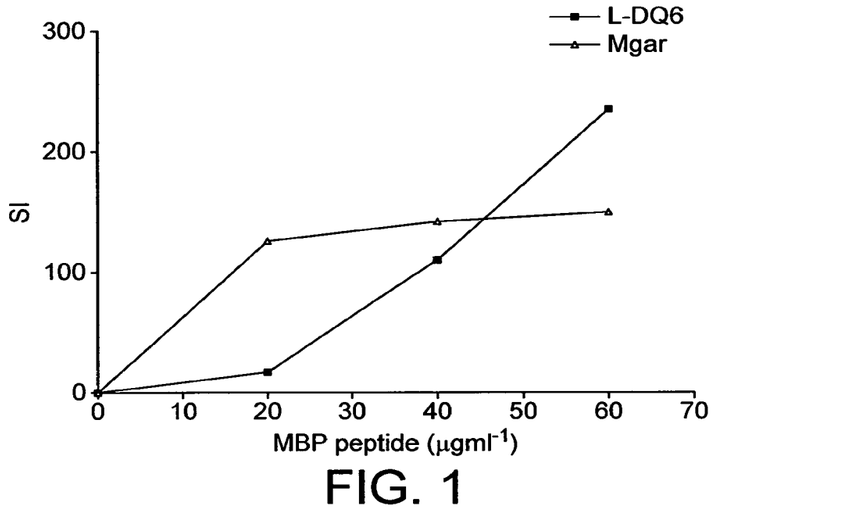
FIG. 1: Presentation of MBP 30-44 by HLA-DQ6 to T-cell clone MS 49:D3
Figure 2:
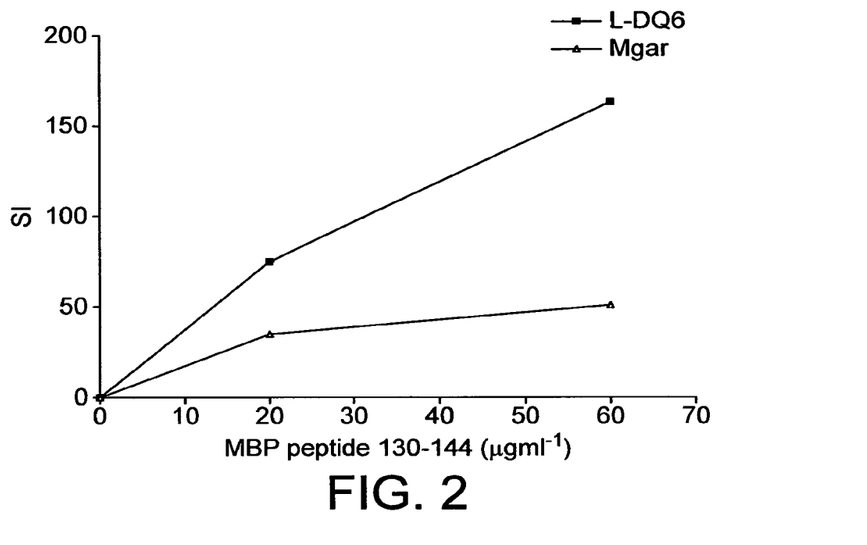
FIG. 2: Presentation of MBP 130-144 by HLA-DQ6 to T-cell clone MS 17:A2

When peptide MBP 30-44 was presented by L cells transfected with HLA-DQ6, T-cell clone MS 49:D3 gave a very strong proliferative response (1.5 fold greater than to Mgar control cells) at the highest peptide concentration (FIG. 1). When MBP 130-144 was presented by L cells transfected with HLA-DQ6 an even stronger response was induced in MS 17:A2 T-cells (3.24 fold increase in proliferation compared to Mgar control cells—FIG. 2).

Figure 3:
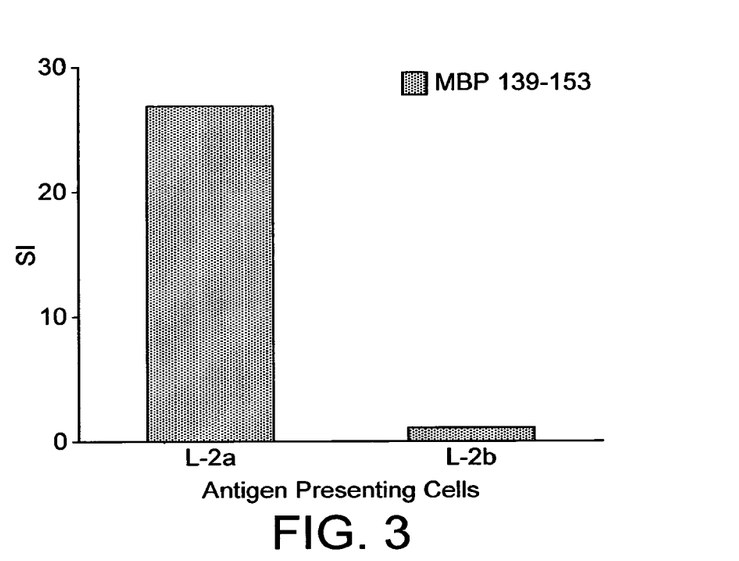
FIG. 3: Presentation of MBP 139-153 by HLA-DR2a and HLA-DR2b transfected L-cells to T-cell clone N5:19

A third T-cell clone isolated from a DR2 individual N5:19 responded to the major epitope MBP 140-154 and to a series of overlapping 15 mer peptides spanning this region (138-156). Peptide 139-153 stimulated proliferation of the N5:19 T-cell clone when presented by HLA-DR2a transfected L-cells, but not HLA-DR2b transfected L-cells (FIG. 3).

Conclusion

T-cell clones isolated from HLA-DR2 positive individuals respond to HLA-DQ6 restricted MBP T-cell epitopes. This implies that the association of HLA-DR2 with multiple sclerosis is not confined to DR2 restriction of MBP T-cell epitopes but may also be DQ6 restricted.

In the MBP composition of the present invention, two of the peptides are HLA-DQ6 binding (MBP 30-44 and 131-145) and two are HLA-DR2 binding (MBP 140-154 and 83-99). Therefore, peptide therapy with these apitopes may be directed to either HLA-DR2 or HLA-DQ6 individuals.

Example 2—Induction of Tolerance with Apitope MS6 in a HLA:DR2 Transgenic Mouse This study was designed to demonstrate that an apitope (Apitope MS6), when presented by an MHC Class II molecule, can induce immunological tolerance in a humanized mouse model of multiple sclerosis. Apitope MS6 is an apitope selected from within T-cell epitopes of MBP corresponding to MBP 140-154, and is presented by MHC Class II on antigen presenting cells, and can stimulate T-cells without being processed (see WO 03/064464). The mouse model used was transgenic for the human MHC molecule HLA:DR2 (DRB1*1501) (Madsen et al (1999) Nature Genetics 23:343-347).

The induction of anergy or changes in the CD4+ T-cell population in a mouse after administration of an apitope may be monitored by a reduction in T-cell proliferation when challenged with the antigen in vivo.

Peptide Synthesis

Apitope MS6 (MBP peptide 140-154) was synthesised using L-amino acids and standard F-moc chemistry on an Abimed AMS 422 multiple peptide synthesiser.

Mice and Tolerance Induction

HLA:DR2 transgenic mice aged 8-12 weeks were used in the study. The mice were tolerised by pre-treatment with 100 µg of Apitope MS6 in 25 µl of phosphate buffered saline (PBS) or 25 μl PBS alone, by intranasal administration on days −8, −6 and −4 prior to immunisation on day 0.

Following tolerisation, mice were immunised subcutaneously with 100 μl of an emulsion containing an equal volume of Complete Freund's Adjuvant (CFA) and PBS containing 200 μg of Apitope MS6 and 400 μg heat-killed *Mycobacterium tuberculosis*. A control group of mice, previously tolerised with PBS intranasally, were immunised without peptide.

At 10 days post subcutaneous immunisation, draining popliteal and inguinal lymph nodes were removed and T-cell activation was assessed by assaying the proliferation of T-cells in response to various concentrations of Apitope MS6. Proliferation was measured by [$^3$H]-Thymidine incorporation, and expressed as the stimulation index (SI=corrected counts per minute (ccpm) culture containing peptide/ccpm culture without peptide).

Results

Figure 4:
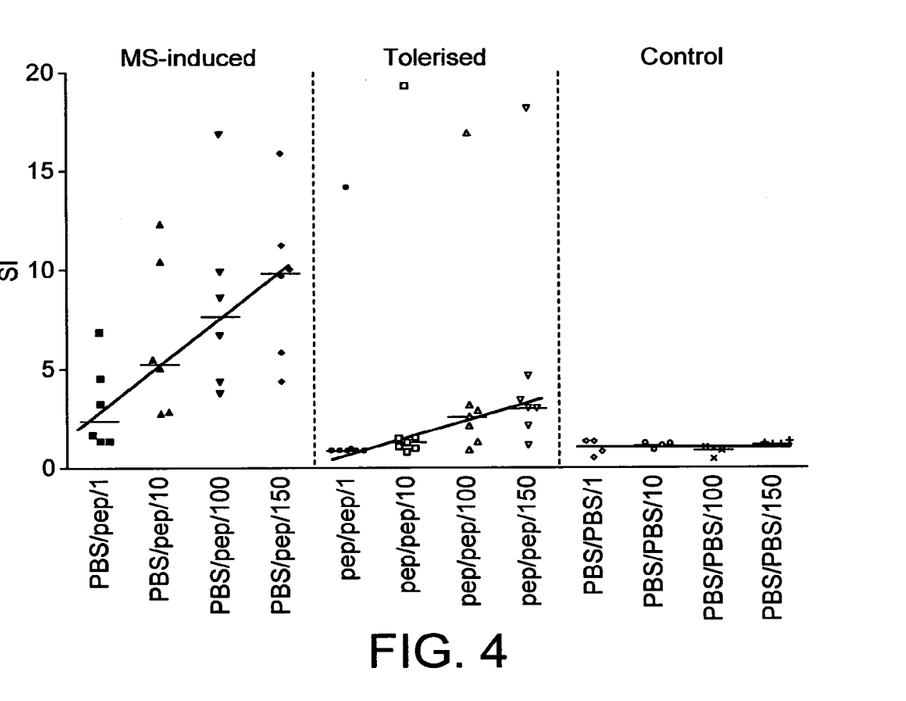
FIG. 4: Proliferative response of lymph node cells following tolerisation with Apitope MS6

Group A mice that were tolerised with PBS and then immunised with Apitope MS6 responded to antigenic stimulation when re-challenged with Apitope MS6 in a dose dependent manner (FIG. 4). With increasing concentration of peptide the SI increased from a median of 2.5 to 10. All the mice in this group demonstrated that PBS administered intranasally could not induce tolerance to Apitope MS6.

In contrast, intranasal pre-treatment with Apitope MS6 had a profound effect on the proliferative response of lymphocytes stimulated with this peptide. Lymphocytes from Group B mice were unable to respond to any significant degree, even at the high peptide concentration of 150 μg/ml (SI median 3, FIG. 4). These data suggest that Apitope MS6 has induced tolerance in lymphocytes from HLA-DR2 mice.

Lymphocytes extracted from mice which had been pre-treated and immunised with PBS (Group C) failed to show any response to Apitope MS6 (FIG. 4). This lack of response to the peptide within Group C confirms that the proliferative response seen in Group A was indeed a response to immunisation with Apitope MS6.

Conclusion

These data support the hypothesis that an MBP peptide (Apitope MS6) that does not require processing and binds to HLA:DR2 MHC Class II molecules, can induce tolerance when administered intranasally.

Example 3—Induction of Tolerance with Apitope MS7 (MBP 83-99) in HLA:DR2 and T-Cell Receptor (MBP) 82-100 Double-Transgenic Mice This study investigates the ability of Apitope MS7 (MBP peptide 83-99) to induce tolerance in double transgenic mice expressing HLA:DR2 together with the T-cell receptor for the HLA: DR2 bound myelin basic protein (MBP) 82-100 peptide.

Splenocytes from these double transgenic animals proliferate in vitro in response to Apitope MS7. Reduction or abrogation of the in vitro splenocyte response to an apitope following its repeated administration in vivo indicates that a state of tolerance has been achieved.

Tolerance induction has been attempted using both the intranasal and subcutaneous/intradermal routes of apitope administration.

Tolerance Induction

Groups of 6 or 7 age (8-12 weeks) and sex matched double transgenic mice were used. In the first experiment one group was treated ten times intranasally with 100 μg Apitope MS7 in 25 μl PBS at regular intervals over a period of three weeks. The control group received PBS alone. In the second experiment the same amount of peptide was given by subcutaneous/intradermal administration in 100 μl of PBS. The control group received the same volume of PBS.

Proliferation Assay

Three days after the last administration of peptide or PBS, the spleens were harvested and cell suspensions prepared. The splenocytes were incubation with 0.5 or 5 μg/ml Apitope MS7, and assessed for proliferation by [$^3$H]-Thymidine incorporation after 48, 72 and 96 hours of culture. Results are expressed as stimulation indices (SI=counts per minute (cpm) of culture containing antigen/counts per minute without antigen).

Cytokine Measurement

In the second experiment, where tolerance induction was induced via the subcutaneous/intradermal route, cell culture supernatants from the splenocytes were collected at 48 and 72 hrs of culture, and assayed for the presence of IFN-γ and interleukin-2 (IL-2) using an enzyme linked immunosorbant assay (ELISA).

Results

Figure 5:
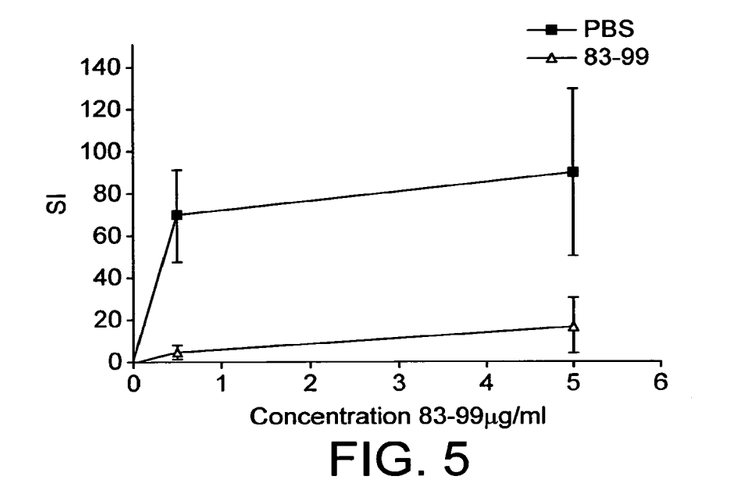
FIG. 5: Proliferation of splenocytes in response to Apitope MS7. Splenocytes obtained from mice treated by intranasal administration of either PBS or Apitope MS7 (83-99)
Figure 6:
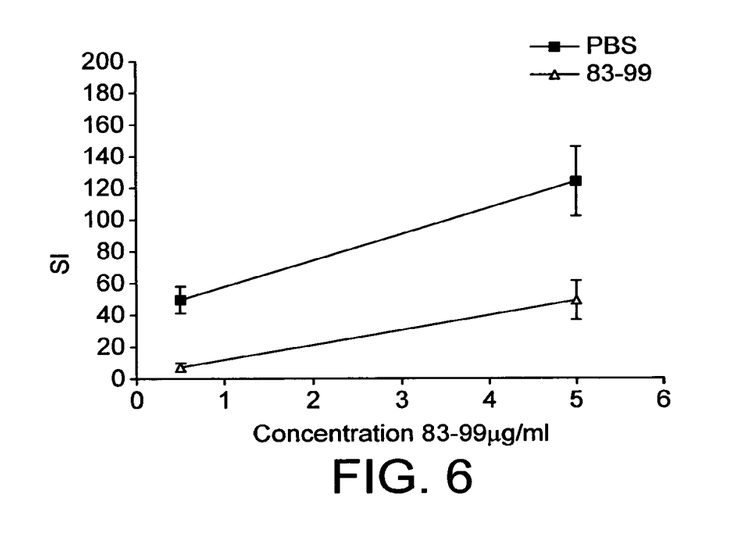
FIG. 6: Proliferation of splenocytes in response to Apitope MS7. Splenocytes obtained from mice treated by subcutaneous/intradermal administration of either PBS or Apitope MS7 (83-99)

At all three time points investigated, splenocytes from mice treated with PBS via both the intranasal and subcutaneous/intradermal route showed strong proliferation to Apitope MS7, the magnitude of the response increasing with peptide concentration. A striking reduction in proliferation was observed in splenocyte cultures from mice treated with Apitope MS7 by both routes of administration. As shown in FIG. 5, after 72 hrs the mean SI observed with cultures containing 5 μg/ml Apitope MS7 was 17 in mice treated intranasally with Apitope MS7. In the corresponding cultures from control mice treated with PBS a mean SI of 89 was observed. Similarly, as shown in FIG. 6 administration of Apitope MS7 by the subcutaneous/intradermal route resulted in a decrease in mean SI from 124 in the PBS treated animals to 49 in animals treated with Apitope MS7.

Figure 7:
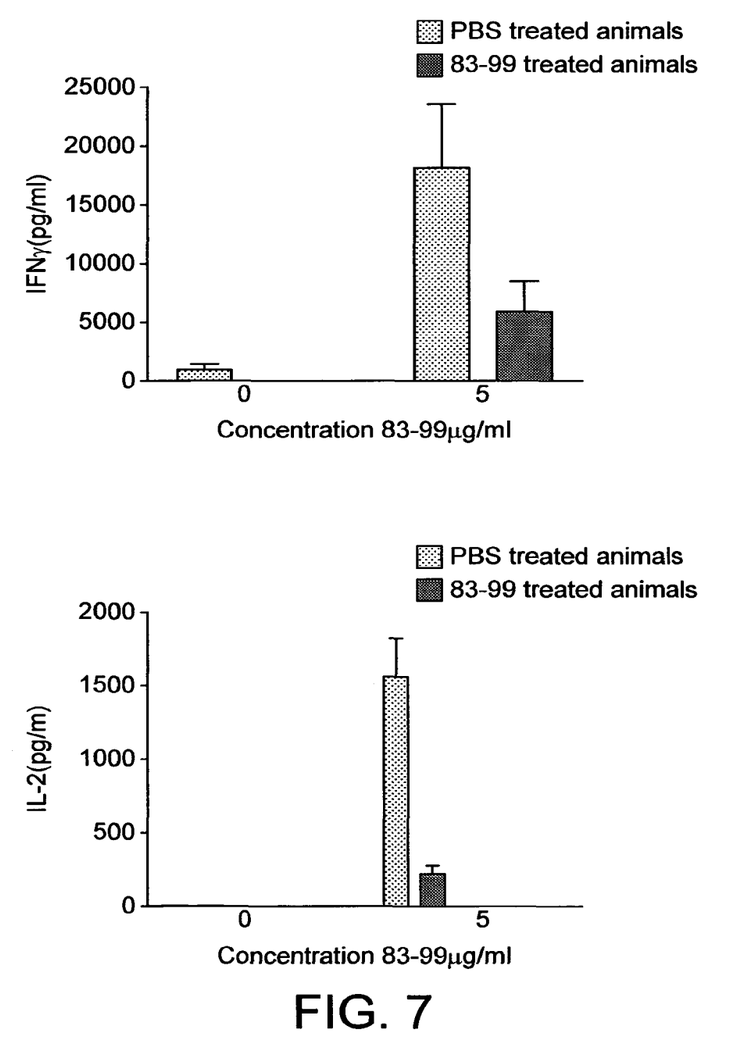
FIG. 7: Production of IFNγ and IL-2 by splenocytes obtained from mice treated by subcutaneous/intradermal administration of either PBS or Apitope MS7 (83-99)

The levels of IFNγ and IL-2 detected in culture supernatants from 48 hr cultures are shown in FIG. 7. The repeated treatment with peptide in vivo is seen to bring about an impressive reduction in secretion of both cytokines, paralleling the reduction in the proliferative response.

Conclusion

These results indicate that tolerance to Apitope MS7 can be successfully induced in a mouse model designed to mimic the human system and supports its potential for use in multiple sclerosis therapy. Furthermore its efficacy is retained when administered by the subcutaneous/intradermal route, the route of choice for humans.

Although the in vivo efficacy of Apitopes MS6 and MS7 has been demonstrated it is not at present possible to demonstrate the efficacy of Apitopes MS1 and MS4. This is because of the lack of transgenic mice expressing the HLA-DQ6 molecule. Mice expressing the molecule have been created, but it has been found that they fail to generate CD4 T-cells in the thymus and do not therefore mount an immune response to antigen in the context of HLA-DQ6.

Example 4—Dose Escalation Study with a Composition of Four MBP Peptides

The combination of four peptides (MBP 30-44, 131-145, 140-154 and 83-99) was used in an open-label, dose-escalation study of ATX-MS-1467 in patients with secondary progressive multiple sclerosis.

Patients were monitored at four weeks and three months after the final study dose for visual acuity (i.e. reduction in optic neuritis), immunological parameters and inflammation in the CNS.

Example 4A—Monitoring Visual Acuity

Optic Neuritis (ON) is an inflammation, with accompanying demyelination, of the Optic Nerve serving the retina of the eye. ON is one of the most frequently presenting symptoms of multiple sclerosis, and is the most common symptom at onset of MS.

Typical symptoms of ON include: blurring of vision, loss of visual acuity, loss of some or all colour vision, complete or partial blindness and pain behind the eye.

Figure 8:
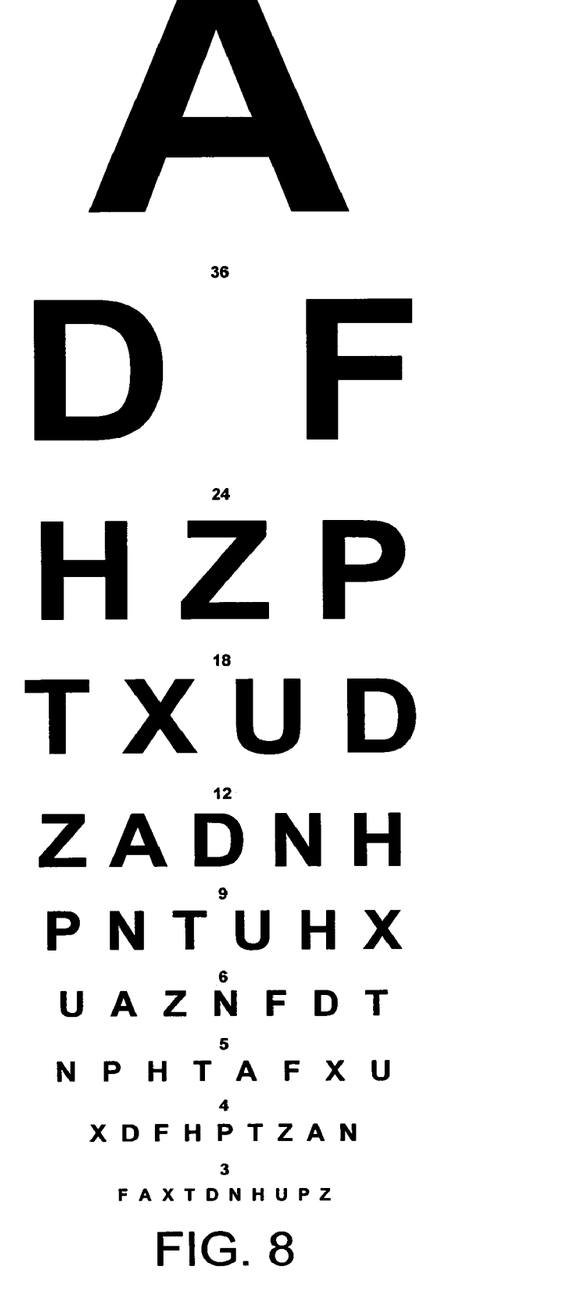
FIG. 8: Example of Snellens chart

The effect of treatment with ATX-MS-1467 on optic neuritis resulting from the neuroinflammatory process involved in MS was investigated. ATX-MS-1467 was given following the dose-escalation protocol outlined above, then one month following treatment the patient's visual acuity was tested using a standard Snellens chart (FIG. 8).

The results show a clinically significant improvement in visual acuity one month post treatment. This was demonstrated in analysis of the initial visual acuity examination at screening compared to the one month follow up test. Initial screening sight measurements of 6/24 and 6/9 (in right and left eyes respectively) improved to 6/9 (right eye) and 6/6 (left eye) post treatment. The patient's eyesight had previously been unchanged for the past two years.

Example 4B—Monitoring Immunological Parameters

As explained above, the effect of peptide therapy with a cocktail containing four Apitope™ peptides from myelin basic protein (ATX-MS-1467) has been investigated on MS patients. Each patient was screened at entry into the trial, up to 14 days prior to the first dose (visit 1). The first dose of 25 µg of ATX-MS-1467 was given on visit 2, 50 µg on visit 3, 100 µg on visit 4, 400 µg on visit 5 and 800 µg on both visits 6 and 7. Further examinations were conducted at one month and three month follow-ups (visits 8 & 9). The following table summarises the protocol and shows the number of visits to the clinical made by each patient along with the dose of peptide and blood sampling.

TABLE 1

| VISIT NUMBER | DOSE OF ATX-MS-1467 (µg) | COMMENT |
|---|---|---|
| 1 | — | Pre-screening visit. 50 ml blood sample collected for immunology |
| 2 | 25 | No immunology sample collected |
| 3 | 50 | 50 ml blood sample for immunology |
| 4 | 100 | 50 ml blood sample for immunology |
| 5 | 400 | 50 ml blood sample for immunology |
| 6 | 800 | 50 ml blood sample for immunology |
| 7 | 800 | 50 ml blood sample for immunology |
| 8 | — | 50 ml blood sample for immunology taken four weeks post visit 7 |

Blood samples were collected at visits 1 and visits 3 to 9 and tested for immune responses to various antigens including purified protein derivative (PPD) of *Mycobacterium tuberculosis*, as a positive control, purified human myelin basic protein (MBP) and ATX-MS-1467. The immune responses to be measured include in vitro T-cell proliferation, secretion of cytokines into tissue culture supernatants and generation of cytokine RNA.

Results

Figure 9:
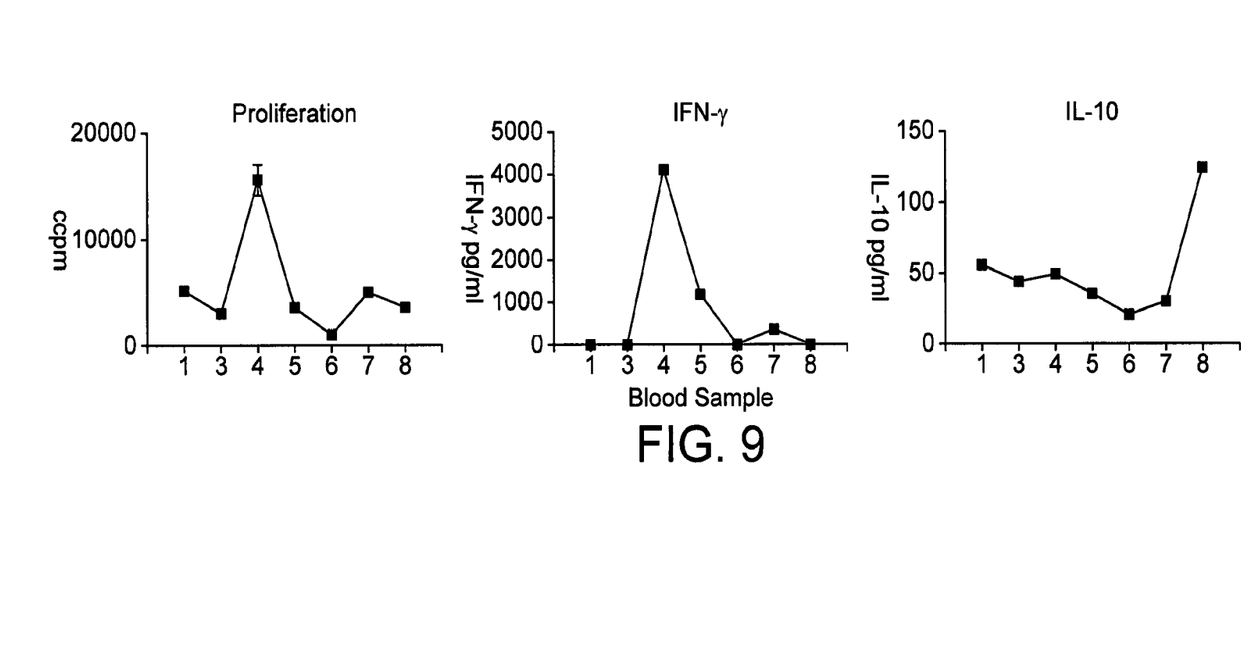
FIG. 9: Patient PBMC responses to human myelin basic protein (MBP)

A significant response to MBP was seen, with a peak in proliferation at visit 3 (FIG. 9). This correlated with a peak in secretion of interferon gamma. Importantly, however, the level of interferon gamma secretion fell after the third visit and was at background level by visit 8. IL-10 levels did not change significantly until visit 7 at which point there was a significant increase in secretion of this cytokine. Levels of IL-4, IL-5 and TNF alpha were close to background in response to MBP at all time points.

Figure 10:
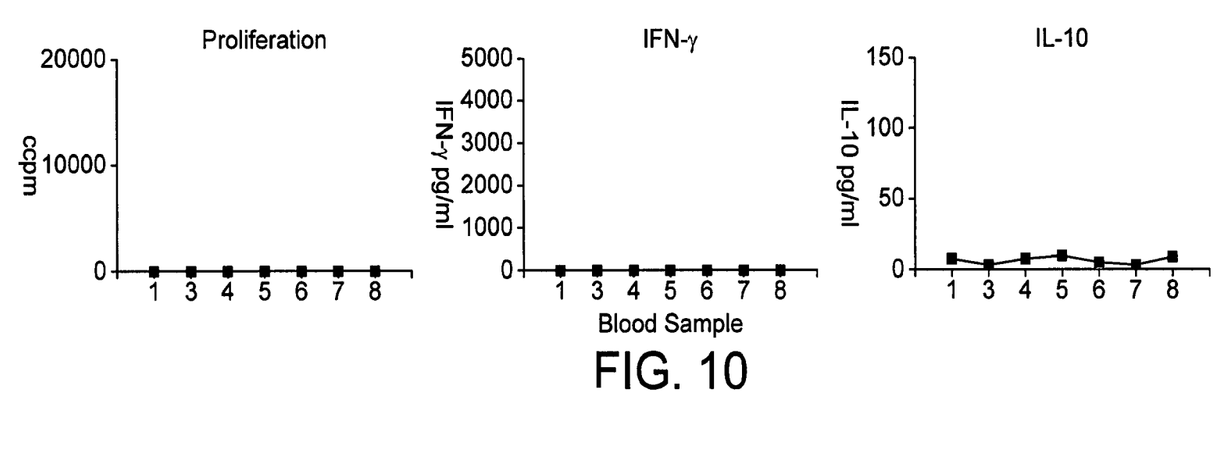
FIG. 10: Patient PBMC responses to ATX-MS-1467

No proliferative response or increased cytokine response was observed to ATX-MS-1467 (FIG. 10).

Conclusion

A response to MBP was observed at visit three demonstrating a heightened secretion of IL-2 and interferon gamma, correlating with a peak in proliferation at this time point. This increase in response is thought to be attributable to the administration of peptides.

Importantly, however, the transient increase in cytokine secretion was followed by a return to baseline levels of interferon gamma. There was also a significant increase in IL-10 secretion following the second administration of ATX-MS-1467 at the highest dose. It has previously been reported that, in animal models, specific immunotherapy with synthetic peptides is effective and results in the induction of IL-10 secreting regulatory T cells. The induction of IL-10 secreting regulatory T cells in mice involves a transient response to peptides with secretion of interferon gamma at low levels (Burkhart et al., 1999 Int Immunol 11: 1625-1634; Sundstedt et al., 2003 J Immunol 170:1240-1248). This is followed by a decrease in interferon gamma and a concomitant increase in IL-10. The kinetics of cytokine secretion displayed following treatment with ATX-MS-1467 effectively reproduces the pattern previously observed in experimental mice, suggesting that ATX-MS-1467 may induce IL-10 secreting regulatory T cells.

Example 4C—Response to MBP is Significantly Down Regulated by Treatment with ATX-MS-1467

Six patients with secondary progressive multiple sclerosis (SPMS) were enrolled into, and completed, a Phase I/IIa clinical trial following the dose-escalation protocol given in Example 4B.

HLA-genotyping showed that the six patients enrolled in the trial represented a wide range of HLA haplotypes, including the MS associated HLA-DR15 haplotype. The broad HLA-DRB1 distribution represented by patients enrolled in this trial implies that ATX-MS-1467 will be safe and well tolerated in MS patients irrespective of their HLA-DR genotype.

Treatment of patients with ATX-MS-1467 did not generate anti-peptide antibodies. This indicates that the use of ATX-MS-1467 is safe and correlates with the lack of injection site complications or allergic manifestations associated with the trial.

Figure 11:
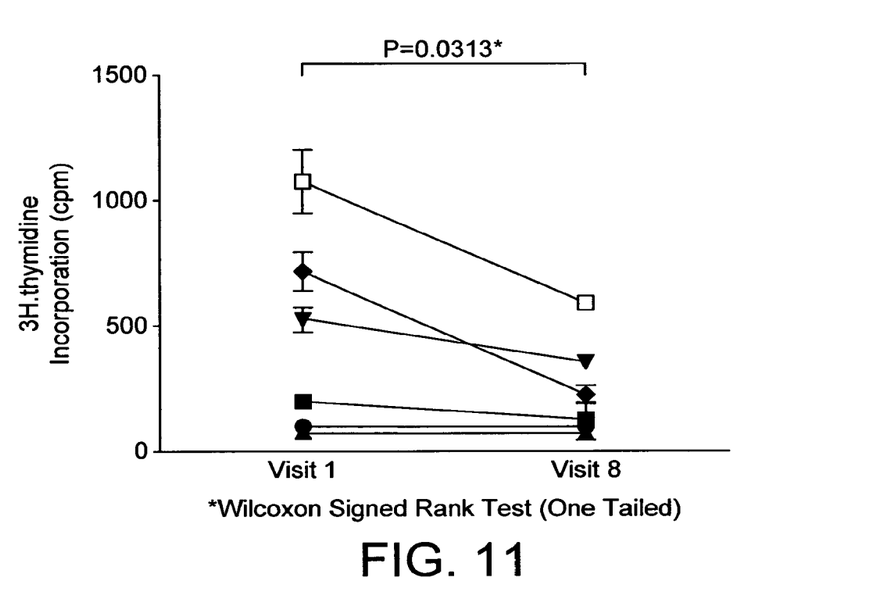
FIG. 11: Comparison of the T cell proliferative response to MBP prior to (visit 1) and following (visit 8) treatment with ATX-MS-1467

A thorough analysis of T cell responses showed that:
a) Treatment with ATX-MS-1467 did not have a non-specific, immunosuppressive effect. This is clearly shown by the fact that the immune response to purified protein derivative, an antigen from *mycobacterium tuberculosis*, was maintained (data not shown).

b) Treatment with ATX-MS-1467, using this protocol, did not lead to an aggressive immune response either to ATX-MS-1467 or myelin basic protein (data not shown).

c) Comparison of the T cell proliferative response prior to (Visit 1) and following (Visit 8) treatment with ATX-MS-1467 revealed a significant reduction in the response to myelin basic protein (FIG. 11). The three individuals who responded to MBP at V1 all showed a reduction in the response to the protein by V8. Taking all of the patients together there is evidence for a significant reduction in the response to MBP from V1 to V8 (P=0.0313).

Materials and Methods
Formulations and Dosages

Each of the four peptides is manufactured independently under contract using solid phase peptide synthesis, and purified using HPLC. They are stored lyophilised.

ATX-MS-1467 is a 1:1:1:1 mixture of Apitopes MS1, MS4, MS6 and MS7 in phosphate buffered saline for intradermal administration.

Two strengths of ATX-MS-1467, designated ATX-MS-1467A and ATX-MS-1467B containing 4 mg/ml and 0.5 mg/ml of peptide, respectively were prepared to allow dose escalation. The regime employs five dose-escalating injections (25, 50, 100, 400 and 800 µg total dose) given 7 to 14 days apart. The patients then receive a second 800 µg dose 7 to 14 days following the first 800 µg dose.

After receiving all six doses of study medication, the patient is assessed at four-weeks and at 3 months after the final study dose.

Visual Acuity Test

A standard size Snellens chart for testing at 6 meters is used, with back light illumination and patient sitting at 6 meters distance (FIG. 8).

Each eye is examined separately for the lowest line on the chart that the patient is able to read. This is then denoted as Visual acuity=6/(the line which the patient has read).

Immunoassays
i) T-Cell Proliferation:

Cryopreserved PBMC are set up in 1 ml cultures containing $1.5 \times 10^6$ cells in α-MEM in 48 well tissue culture plates (Nunc International, Costar, Corning Inc. New York USA). Responses to MBP and peptide antigens at various concentrations are monitored over a period of 10 days. Control wells contain no antigen. After 20 hrs or 2, 4, 6, 8 and 10 days of culture, duplicate 100 µl aliquots of cell suspension are removed from each 1 ml culture to measure proliferation in response to antigen by uptake of [$^3$H] thymidine.

ii) Measurement of Secreted Cytokines (IL-2 and IL-4, IL-5, IL-10, TNF-α and IFN): Cytometric Bead Array Assay:

Culture supernatant cytokine levels are determined using the Cytometric Bead Assay (Becton Dickenson Biosciences, Cowley, Oxford, UK) following the manufacturer's instructions. Following acquisition of sample data using the FACS Calibur (BD Biosciences), results are generated in graphical and tabular form using BD CBA software. The minimum quantifiable levels of cytokine are as follows: IL-2 and IL-4 2.6 pgml-1, IL-5 2.4 pgml-1, IL-10 and TNF-α 2.8 pgml-1, IFN-γ 7.1 pgml-1.

Quantitative Real Time PCR to Measure RNA of Cytokines (IL-2, IL-10, IFN-γ and TNF-α)

For analysis of IL-2, IL-10, IFN-γ and TNF-α, PCR reactions are carried out in a final volume of 20 µl containing cDNA, PCR buffer, 6.25 mM $MgCl_2$, 0.4 mM dNTP mix, forward and reverse primers (forward primer concentrations: IL-2 300 nM, IL-10 600 nM, IFN-γ 600 nM, TNF-α 600 nM, reverse primer concentrations: IL-2 600 nM, IL-10 900 nM IFN-γ 900 nM, TNF-α 600 nM), 200 nM FAM-TAMRA probe and 0.05 Uµl-1 Platinum Taq polymerase (Invitrogen). The cycling conditions are as follows: an initial denaturation step at 94° C. for 30 s, followed by 35 cycles with 15 s at 94° C. and 1 min at 60° C. For β-2 microglobulin, the PCR mix described above is supplemented with 0.1 uM forward and reverse primers, 3 mM MgCl2 and quantitated with SYBR Green I (Molecular Probes Inc., X30000 dilution of stock). Following a 1 min denaturation step at 95° C., amplification continues with 35 cycles of 15 s at 94° C., 1 min at 61° C. and 1 min at 72° C. The PCR reactions and fluorescence detection of amplicons generated is performed on an Opticon 2 system (MJ Research, USA). Baseline fluorescence is established by taking measurements from cycle 1 to 10. Ct values are calculated by determining the point at which the fluorescence exceeds 8-10 times the standard deviation of the baseline. Samples are assayed in duplicate and copy number calculated from a standard curve for each target DNA. Differences in RNA input copy number and cDNA synthesis are corrected by normalizing cytokine expression to the expression of β-2 microglobulin.

HLA Typing

Analysis of HLA gene expression is performed by a standard single-strand conformation polymorphism, polymerase chain reaction technique on DNA extracted from peripheral blood leukocytes. The HLA-type of each patient is used for interpretation of the results of immunological assays.

Serum Anti-Peptide Antibody Assays 96 well plates are coated with 1-10 µg/ml of each apitope MS1, MS4, MS6 or MS7 at pH 9.6 overnight at 4° C. Plates are washed four times with phosphate-buffered saline, pH 7.2, 0.05% Tween (PBS-Tween) and the wells blocked with 5% FCS in PBS for 1 h at room temperature. Sera are diluted 1:100 in PBS-Tween and incubated in duplicate wells for one hour at room temperature. After 4 washes, Goat anti-human IgG-horseradish peroxidase conjugate (Sigma) diluted 1:12 000 in PBS is added to each well and the plates incubated for one hour at room temperature. After 4 washes 0.4 mg/ml of o-phenylenediamine dihydrochloride (Sigma) plus 30% hydrogen peroxide is added and incubated at room temperature for 15-20 min. Colour development is stopped with 2.0 M $H_2SO_4$ (50 µl) and optical density values (ODs) measured at 490 nm with an ELISA plate reader. Results are reported as OD for 1:100 diluted sera.

MRI Scan

Inflammation in the CNS is investigated using a gadolinium-enhanced MRI scan. The volume and number of enhancing lesions is examined and compared with the baseline scan.

Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry or biology or related fields are intended to be covered by the present invention. All publications mentioned in the above specification are herein incorporated by reference.

The invention claimed is:

1. A method of reducing or ameliorating a symptom of multiple sclerosis or optic neuritis in a subject having multiple sclerosis or optic neuritis, the method comprising a step of administering to the subject a composition of myelin basic protein peptides, wherein the myelin basic protein peptides of the composition consist of myelin basic protein peptides MBP 30-44, MBP 83-99, MBP 131-145 and MBP 140-154.

2. The method according to claim 1, wherein the composition further comprises a pharmaceutically acceptable excipient.

3. The method according to claim 1, wherein the subject has multiple sclerosis.

4. The method according to claim 1, wherein the subject has optic neuritis.

5. The method according to claim 1, in which the composition is administered to the subject following a dose-escalation protocol.

6. The method according to claim 1, wherein the composition is administered to an HLA-DQ6 or HLA-DR2 positive subject.

* * * * *

SEQUENCE LISTING

```
<160> NUMBER OF SEQ ID NOS: 4

<210> SEQ ID NO 1
<211> LENGTH: 15
<212> TYPE: PRT
<213> ORGANISM: Homo sapiens

<400> SEQUENCE: 1

Pro Arg His Arg Asp Thr Gly Ile Leu Asp Ser Ile Gly Arg Phe
1               5                   10                  15

<210> SEQ ID NO 2
<211> LENGTH: 17
<212> TYPE: PRT
<213> ORGANISM: Homo sapiens

<400> SEQUENCE: 2

Glu Asn Pro Val Val His Phe Phe Lys Asn Ile Val Thr Pro Arg Thr
1               5                   10                  15

Pro

<210> SEQ ID NO 3
<211> LENGTH: 15
<212> TYPE: PRT
<213> ORGANISM: Homo sapiens

<400> SEQUENCE: 3

Ala Ser Asp Tyr Lys Ser Ala His Lys Gly Phe Lys Gly Val Asp
1               5                   10                  15

<210> SEQ ID NO 4
<211> LENGTH: 15
<212> TYPE: PRT
<213> ORGANISM: Homo sapiens

<400> SEQUENCE: 4

Gly Phe Lys Gly Val Asp Ala Gln Gly Thr Leu Ser Lys Ile Phe
1               5                   10                  15
```

UNITED STATES PATENT AND TRADEMARK OFFICE
CERTIFICATE OF CORRECTION

PATENT NO. : 9,775,880 B2  
APPLICATION NO. : 15/173018  
DATED : October 3, 2017  
INVENTOR(S) : David Wraith et al.

Page 1 of 1

It is certified that error appears in the above-identified patent and that said Letters Patent is hereby corrected as shown below:

On the Title Page

Item (54) and in the Specification, Column 1, Line 1, "BASIS" should be -- BASIC --.

Signed and Sealed this  
Eleventh Day of September, 2018

Andrei Iancu  
*Director of the United States Patent and Trademark Office*